United States Patent [19]

Yasue

[11] Patent Number: 5,550,372

[45] Date of Patent: Aug. 27, 1996

[54] APPARATUS AND METHOD FOR ANALYZING FOREIGN MATTER ON SEMICONDUCTOR WAFERS AND FOR CONTROLLING THE MANUFACTURING PROCESS OF SEMICONDUCTOR DEVICES

[75] Inventor: Takao Yasue, Itami, Japan

[73] Assignee: Mitsubishi Denki Kabushiki Kaisha, Tokyo, Japan

[21] Appl. No.: 543,826

[22] Filed: Oct. 16, 1995

[30] Foreign Application Priority Data

Oct. 24, 1994 [JP] Japan ................................ 6-258399

[51] Int. Cl.⁶ .................................................. H01J 37/256
[52] U.S. Cl. ........................................ 250/310; 250/307
[58] Field of Search ........................................ 250/310, 307

[56] References Cited

U.S. PATENT DOCUMENTS

| | | | |
|---|---|---|---|
| 4,037,101 | 7/1977 | Okumura et al. | 250/310 |
| 4,857,731 | 8/1989 | Tagata | 250/310 |
| 5,233,191 | 8/1993 | Noguchi et al. | 250/307 |

OTHER PUBLICATIONS

Kawahigashita, Takashi; "Handoutai Hyoka Gijitsu (Semiconductor Technique)" pp. 166–172. Sangyo–Tosho, Feb. 28, 1989.

Usami, Akira; "100 Rei ni Miru Handoutai Hyoka Gijutsu (Semiconductor Evaluation Techniques: 100 cases)"; May 1, 1988.

*Primary Examiner*—Jack I. Berman
*Attorney, Agent, or Firm*—Leydig, Voit & Mayer

[57] ABSTRACT

A device for analyzing foreign matter on semiconductor wafers is provided, which is capable of analyzing a great deal of foreign matter rapidly without requiring the higher level decision capabilities of a skilled analyst. The device for analyzing foreign matter on semiconductor wafers includes a scanning electron microscope (SEM) which obtains the composition ratios of each element of a plurality of foreign matter adhered to semiconductor wafers. A foreign matter plotting section is provided to obtain the distribution of the composition ratios of the plurality of foreign matter on the basis of a result obtained by the SEM. A foreign matter classifying process section classifies the plurality of foreign matter on the basis of the distribution. A foreign matter identifying process section compares the foreign matter classification result with data stored in advance in a foreign matter data base, thereby identifying the foreign matter type.

6 Claims, 11 Drawing Sheets

SECONDARY ELECTRON
IMAGE BY SEM

EPMA ANALYSIS SPECTRUM OF
FOREIGN MATTER A

EPMA ANALYSIS SPECTRUM OF
FOREIGN MATTER B

SCATTER DIAGRAM OF
PRINCIPAL COMPONENTS
OF FOREIGN MATTER A

SCATTER DIAGRAM OF
PRINCIPAL COMPONENTS
OF FOREIGN MATTER B

SCATTER DIAGRAM PRINCIPAL COMPONENTS
OF FOREIGN MATTERS OF WHICH THE NUMBER IS N
AFTER ANALYSIS

SECONDARY ELECTRON IMAGE BY SEM

EPMA ANALYSIS SPECTRUM OF FOREIGN MATTER A

EPMA ANALYSIS SPECTRUM OF FOREIGN MATTER B

APPARATUS AND METHOD FOR ANALYZING FOREIGN MATTER ON SEMICONDUCTOR WAFERS AND FOR CONTROLLING THE MANUFACTURING PROCESS OF SEMICONDUCTOR DEVICES

BACKGROUND OF THE INVENTION

1. Field of the Invention

The present invention relates to an analyzer for analyzing the foreign matter on a semiconductor wafer or on the pattern of a semiconductor device formed on the semiconductor wafer, a control apparatus for controlling the manufacturing process of the semiconductor devices, a method for analyzing the foreign matter on the devices and a method for controlling the manufacturing process as applied to the analyzer and control apparatus.

2. Description of the Related Art

The minute foreign matter which adheres to a semiconductor wafer or to the pattern of a semiconductor device formed on a semiconductor wafer (including the foreign matter below the thin film formed on a semiconductor wafer) is a major factor in the low yield of the manufacturing process of semiconductor devices such as IC's or LSI's. In order to prevent the foreign matter from adhering to the wafer, it is important to identify the source of the foreign matter, and to take measures to prevent pollution. It is therefore necessary to analyze the composition ratio and the condition of the foreign matter.

Electron Probe Microanalysis (EPMA) using a Scanning Electron Microscope (SEM) is one of the conventional methods for such analysis. EPMA is also called X-Ray Microanalysis (XMA) in Japan.

The EPMA technique was developed in the latter half of the 1960's. It applies an electron beam to a test piece so as to detect characteristic X-rays which are generated from the foreign matter on the surface of the test piece, thereby identifying the composition ratio of the foreign matter. EPMA was described in detail in, for example, Takashi Kawahigashita's "Handoutai Hyoka Gijutsu (Semiconductor Evaluation Technique)", pg. 166–172, Sangyo-Tosho, and Akira Usami's "100 Rei ni Miru Handoutai Hyoka Gijutsu (Semiconductor Evaluation Techniques: 100 cases). There are two types of EPMA, i.e., wavelength dispersive type and energy dispersive type. The Energy dispersive type is superior to the wavelength dispersive type in both through-put and simplicity. Data as measured by energy dispersive type EPMA is described below.

FIG. 16 illustrates a typical secondary electron image by SEM in which two pieces of foreign matter A and B are adhered to the surface of semiconductor wafer 101. In the EPMA method, the foreign matter to be analyzed is indicated on the display in advance. Then, an electron beam is focused on and applied to the each bit of foreign matter respectively. The X-ray spectrum radiated by the foreign matters are displayed and analyzed respectively.

FIG. 17 illustrates a typical EPMA analysis spectrum of the foreign matter A. In this figure, the horizontal axis indicates X-ray energy the units of which are electron volts and the vertical axis indicates X-ray intensity the units of which unit are counts per second (CPS). The graph in this figure has a first peak of X-ray intensity $I_1$ at X-ray energy $E_1$ and a second peak of X-ray intensity $I_2$ at X-ray energy $E_2$. The first peak indicates that element X is contained in foreign matter A. The second peak indicates that element Y is also contained in foreign matter A. $I_1$ and $I_2$ are in a ratio of approximately 2:1. Thereby, FIG. 17 indicates that the composition ratio of elements X and Y in foreign matter A is approximately a 2:1 ratio, though the relationship between X-ray intensity and the composition ratio does not always have linearity because of various compensations.

FIG. 18 indicates a typical EPMA analysis spectrum of foreign matter B. The graph in this figure has a first peak of X-ray intensity $I_2$ at X-ray energy $E_3$ and a second peak of X-ray intensity $I_2$ at X-ray energy $E_3$. The first peak indicates that element Z is contained in foreign matter B. The second peak indicates that element Y is also contained in foreign matter B. The height of the first peak is approximately the same as the height of the second peak. Thereby, FIG. 18 indicates that the composition ratio of elements Z and Y in foreign matter B is approximately a 1:1 ratio.

Thus, on the basis of FIG. 17 and FIG. 18, the composition ratio and the element type of the elements which compose foreign matter A and B can be obtained. Based on these results, an analyst can identify what type of foreign matter A and B are. If the type is identified, the generation process of the foreign matters can also be identified.

As mentioned above, according to conventional methods of foreign matter analysis, an analyst obtains the composition ratio and the element type of the elements which composes the foreign matter based on spectral analysis, thereby identifying the type of foreign matter directly.

However, as the types of foreign matter adhering to a test piece increases, the types and the composition ratio of the elements which compose the foreign matter become much more varied. Consequently, according to the conventional methods of foreign matter analysis, data is very complex and thus difficult to explain. Also, it is very difficult to find the generation process of the foreign matter.

Thus, the conventional methods of foreign matter analysis have a low through-put and require a great deal of time and the skilled valuation of an analyst.

SUMMARY OF THE INVENTION

With a view to solving above-described problems, an object of the present invention is to provide an analyzer for analyzing foreign matter on semiconductors which can analyze many pieces of foreign matter rapidly without necessitating the high-level evaluation of a skilled analyst and a method for analyzing this foreign matter. A further object of the present invention is to provide a control apparatus for controlling the manufacturing process of semiconductor devices and a method for controlling the manufacturing process thereof.

To achieve this object, according to the present invention, there is provided an analyzer for analyzing this foreign matter on a semiconductor wafer comprising an analyzing section for obtaining composition ratios of the foreign matter which adheres to a semiconductor wafer;

a foreign matter distribution generation section for obtaining distributions of each component of the foreign matter on the basis of the analysis obtained by the analyzing section;

a foreign matter classifying section for classflying the foreign matter on the basis of the distributions obtained by the foreign matter distribution generation section; and a foreign matter identifying section for comparing the classification results obtained by the foreign matters classifying section with predetermined foreign matter data, and identifying the foreign matter type.

DESCRIPTION OF THE PREFERRED EMBODIMENTS

Embodiment 1

The first embodiment of the present invention will now be described with reference to the drawings.

Figure 1:
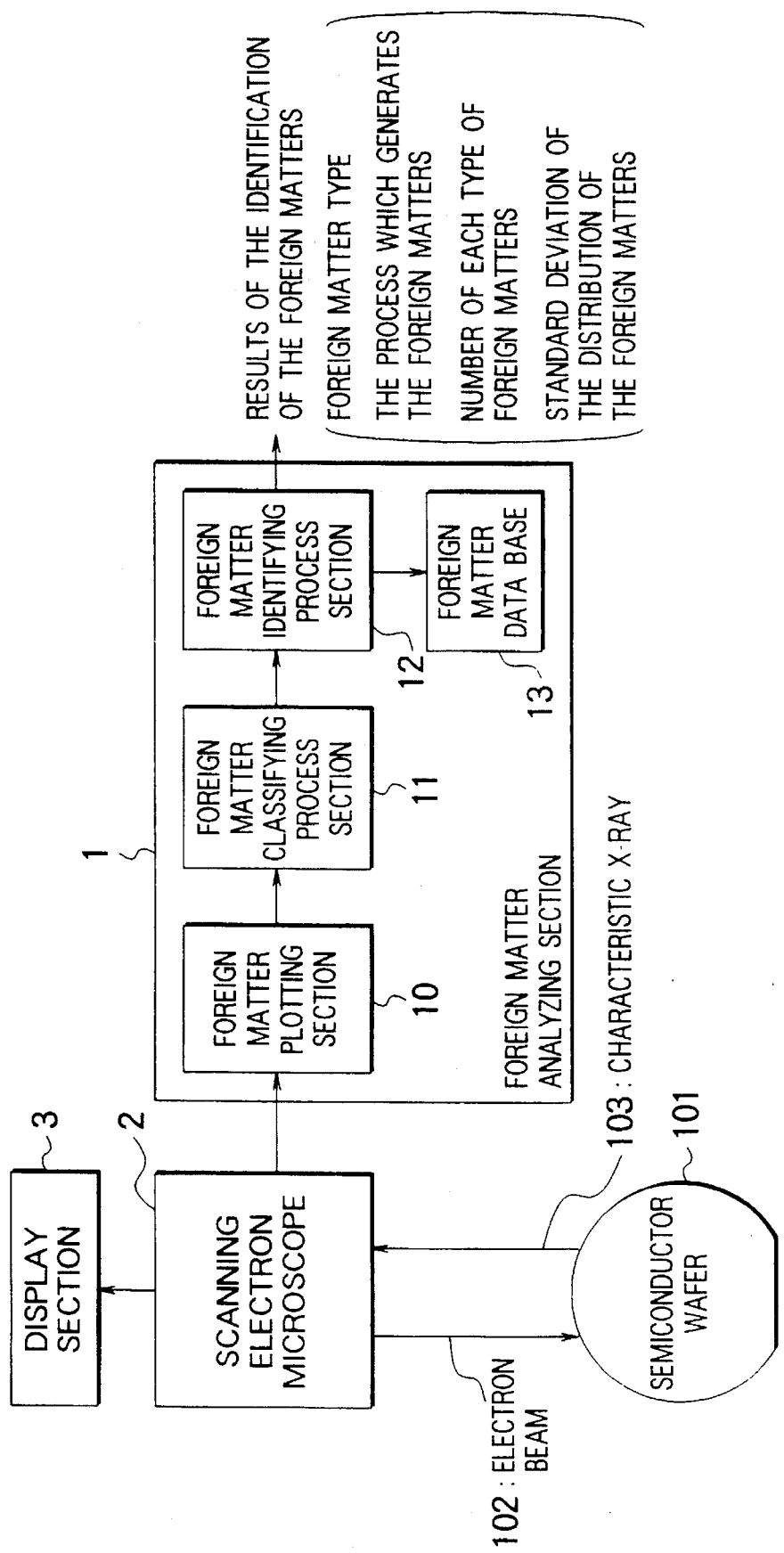
FIG. 1 is a functional block diagram showing the construction of a first embodiment of the foreign matter analyzing system of the present invention.

FIG. 1 is a functional block diagram showing the construction of the foreign matter analyzing system of embodiment 1. In FIG. 1, a foreign matter analyzing section 1 classifies foreign matter on semiconductor wafer 101 and identifies foreign matter type and the process which generates them, outputting the results of the identification of the foreign matter. The foreign matter analyzing section 1 outputs foreign matter type, the process which generates them, the number of each type of foreign matter and the standard deviation of their distribution. The foreign matter analyzing section 1 comprises a foreign matter plotting section 10 which plots the number of foreign matter in the space formed by the coordinate axes of the composition ratio of each type of element on the basis of the EPMA spectrum, a foreign matter classifying process section 11 which classifies the foreign matters in several categories on the basis of the plotted data and a foreign matter identifying process section 12 which compares the results of classification obtained by the foreign matter classifying process section 11 with the foreign matter data pre-stored in the foreign matter data base 13, thereby obtaining the foreign matter type, the process which generates the foreign matter, the number of each kind of foreign matter and the standard deviation of the distribution of the foreign matter.

A scanning electron microscope. (SEM) 2 applies an electron beam to a test piece and detects the characteristic X-ray radiated from the foreign matter on the surface of the test piece, thereby identifying the composition of the foreign matter. As illustrated in FIG. 1, SEM 2 applies electron beam 102 to semiconductor wafer 101, here used as a test piece, and thereby detects characteristic X-ray 103 from the semiconductor wafer 101. A display section 3 displays the surface image of the test piece observed by SEM 2.

Figure 2:
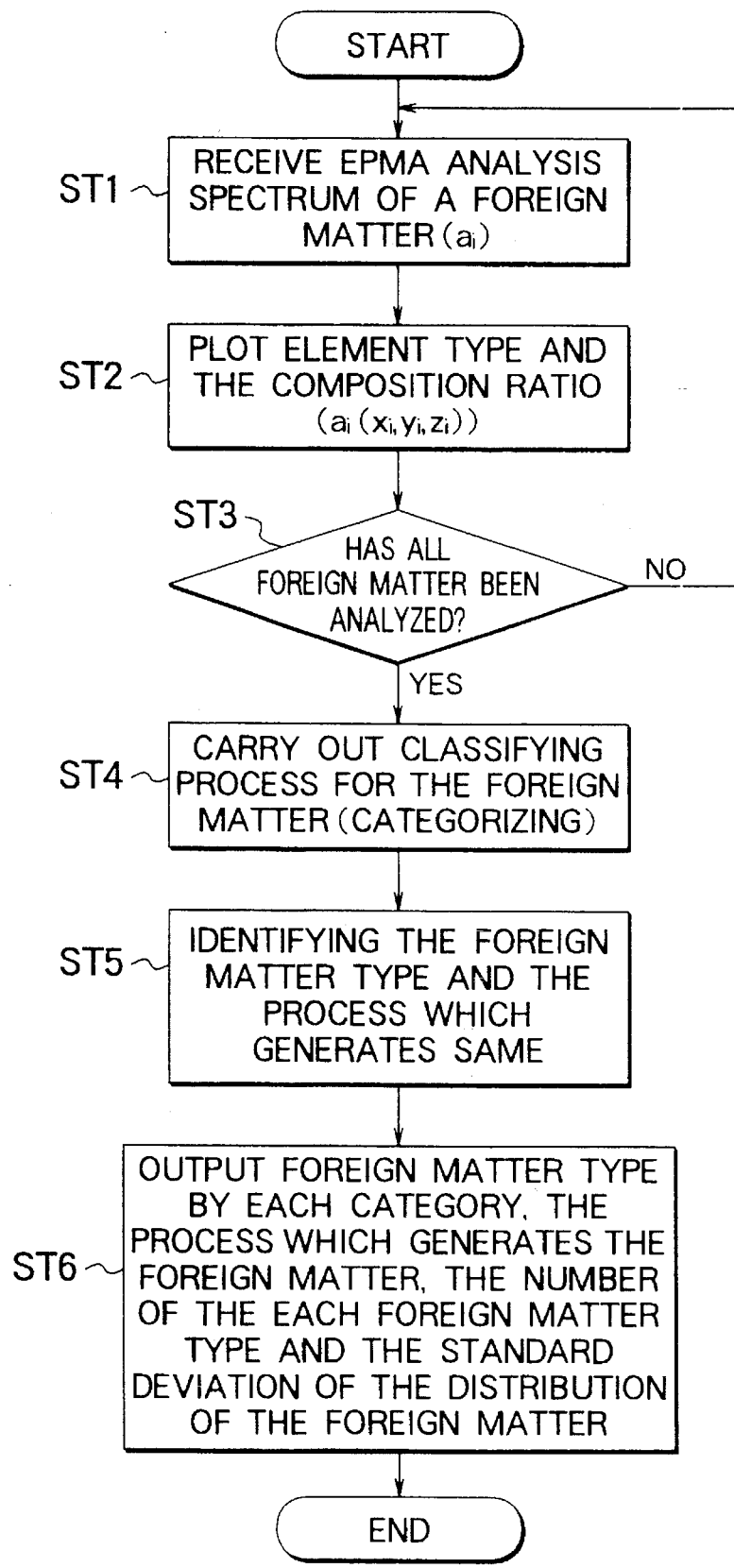
FIG. 2 is a flowchart of the process of the analyzing section of the first embodiment of the present invention.

Next, the operation of the foreign matter analyzing system of embodiment 1 will be explained with reference to the functional block diagram of FIG. 1, the flowchart of FIG. 2 and the drawings of a typical case in FIGS. 3 to 11.

Figure 3:
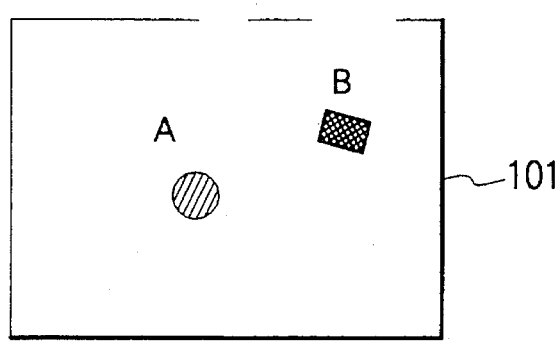
FIG. 3 illustrates a typical secondary electron image of the surface of a semiconductor wafer shown on the display of a first embodiment of the present invention.
Figure 4:
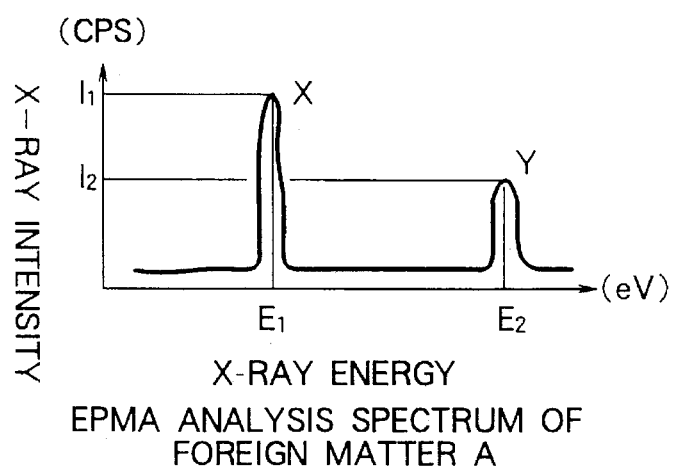
FIG. 4 illustrates a typical EPMA analysis spectrum of foreign matter A of the first embodiment of the present invention.
Figure 5:
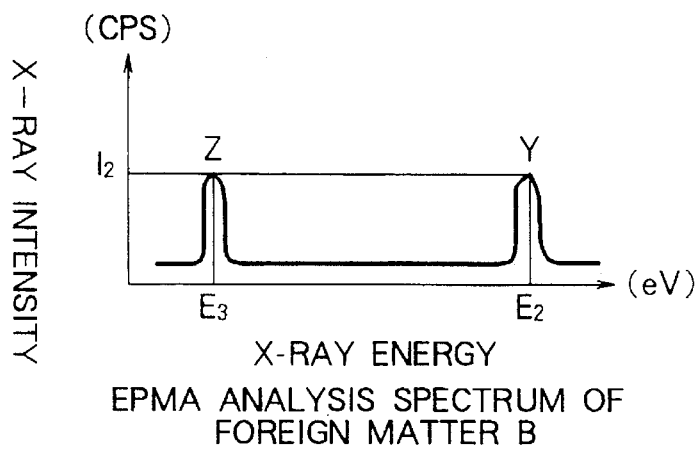
FIG. 5 illustrates a typical EPMA analysis spectrum of foreign matter B of the first embodiment of the present invention.

SEM 2 applies electron beam 402 to the semiconductor wafer 101. Then, the semiconductor wafer 101 radiates secondary electrons and characteristic X-rays 103. Based on the foregoing, SEM 2 makes a secondary electron image and displays it on the display section 3. FIG. 3 is a typical example of a secondary electron image displayed on the display section 3. FIG. 3 illustrates that two pieces of foreign matter, A and B, adhere to the surface of semiconductor wafer 101. On the basis of the image, electron beam 102 is focused first on one then on the other of these bits of foreign matter. The EPMA analysis spectrum of foreign matter A and B illustrated by FIG. 4 and FIG. 5 are obtained by the EPMA method based on the characteristic X-rays 103 radiated by these bits of foreign matter.

The process mentioned above is carried out for all foreign matter. Consequently, the number of EPMA analysis spectrums is the same as the number of bits of foreign matter.

SEM 2 outputs an EPMA analysis spectrum for each foreign matter to the foreign matter analyzing section 1. The foreign matter analyzing section 1 processes the EPMA analysis spectrum in accordance with the flowchart illustrated in FIG. 2.

ST1

The foreign matter plotting section 10 of the foreign matter analyzing section 4 receives an EPMA analysis spectrum of foreign matter $a_i$ (wherein i=1, 2, . . . , n) from SEM 2.

ST2

The foreign matter plotting section 10 of the foreign matter analyzing section 1 obtains the element type and the composition ratio ($a_i$ ($x_i,y_i,z_i$)) of the elements which compose the foreign matter on the basis of the received EPMA analysis spectrum, wherein $x_i$ is the composition ratio of element X, $y_i$ is the composition ratio of element Y, $z_1$ is the composition ratio of element Z.

Element type and the composition ratio are concretely obtained as follows.

FIG. 4 illustrates atypical EPMA analyzing spectrum of foreign matter A illustrated by FIG. 3. In this figure, the horizontal axis indicates X-ray energy the unit of which is electron volts and the vertical axis indicates X-ray intensity the unit of which is counts per second (CPS). The foreign matter plotting section 10 of the foreign matter analyzing section 1 scans the EPMA analysis spectrum in the direction of the horizontal axis so as to obtain peak and energy at the peak of the EPMA analysis spectrum, The graph in this figure has a first peak of X-ray intensity $I_1$ at X-ray energy $E_1$ and a second peak of X-ray intensity $I_2$ at X-ray energy $E_2$. The first peak indicates that element X is contained in foreign matter A. The second peak indicates that element Y is also contained in foreign matter A. $I_1$ and $I_2$ are in a ratio of approximately 2:1.

Thereby, FIG. 4 means that the composition ratio of element X and Y in foreign matter A is in a ratio of approximately 2:1, though the relationship between X-ray intensity and the composition ratio does not always have linearity due to various compensations. Accordingly, element type and composition ratio of elements which compose foreign matter A are obtained as $a_A$ (2, 1, 0). The relationship between X-ray intensity and composition ratio does not always have linearity depending on the elements. In such a case, the composition ratio of element X and Y of FIG. 4 may be in a ratio of 1:1. However, even in this case, we can obtain the composition ratio of foreign matter on the basis of the EPMA analysis spectrum because the composition ratios of foreign matter correspond in a 1:1 ratio, to the X-ray intensity distributions of the analysis spectrum.

Figure 6:
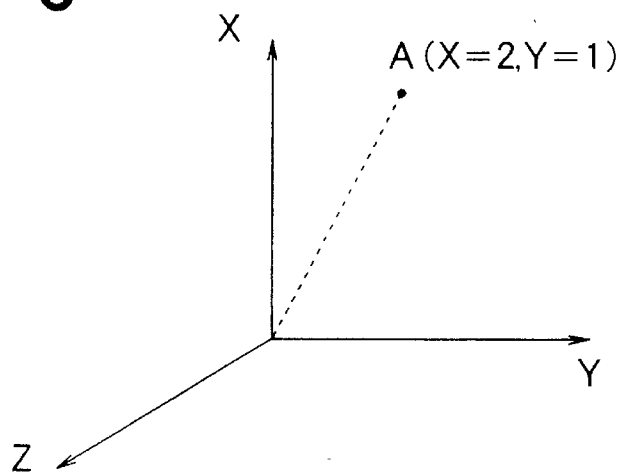
FIG. 6 illustrates the condition of foreign matter A of the first embodiment of the present invention as plotted in the space formed by the coordinates axes of the composition ratio of each type of element.

FIG. 6 illustrates foreign matter A as plotted in the space formed by the coordinate axes of the elements X, Y, Z. Since, in the composition ratio of foreign matter A, the element Z is zero, foreign matter is plotted on X-Y plane. The diagram in which foreign matter is plotted such as in FIG. 6 is called a scatter diagram of principal components.

The composition ratio and element type of the foreign matter B are obtained similarly. According to FIG. 5 which illustrates the EPMA analysis spectrum, there is a first peak of X-ray intensity $I_2$ at X-ray energy $E_3$ and a second peak of X-ray intensity $I_2$ at X-ray energy $E_2$. The first peak indicates that element Z is contained in foreign matter B. The second peak indicates that element Y is contained in foreign matter B. The height of the first peak is approximately the same as the height of the second peak. This means that the composition ratio of elements Z and Y in foreign matter B is in a ratio of approximately 1:1. Consequently, the composition ratio and element type of the elements which compose foreign matter B are obtained as $a_B$ (0, 1, 1).

Figure 7:
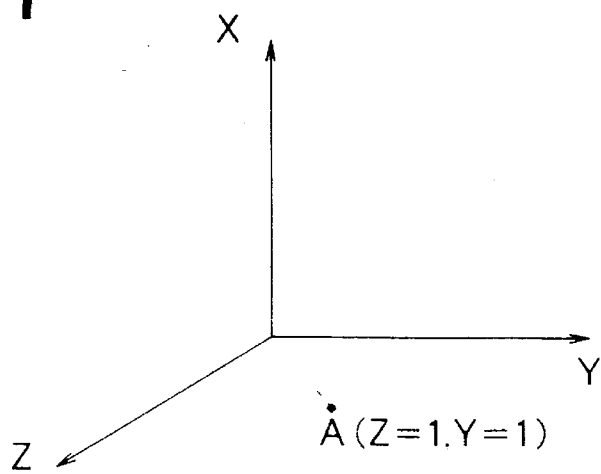
FIG. 7 illustrates the condition of foreign matter B of the first embodiment of the present invention as plotted in the space formed by the coordinates axes of the composition ratio of each type of element.

FIG. 7 also illustrates foreign matter B as plotted in the space formed by the coordinate axes of the elements X, Y, Z. Since in the composition ratio of foreign matter B concerning element X is zero, the foreign matter B is plotted on the Y-Z plane.

ST3

The foreign matter plotting section 10 decides whether all foreign matter has been analyzed. If the analysis is not finished (No), the process returns to step ST1 and the composition ratio and element type of the next foreign matter will be sought.

If the analysis is finished (Yes), the process proceeds to step ST4.

ST4

The foreign matter classifying process section 11 of the foreign matter analysis section 1 classifies the foreign matters (categorizing) on the basis of the analysis results obtained by the processes of ST1 to ST3 for the foreign matters of which the number is n.

Figure 8:
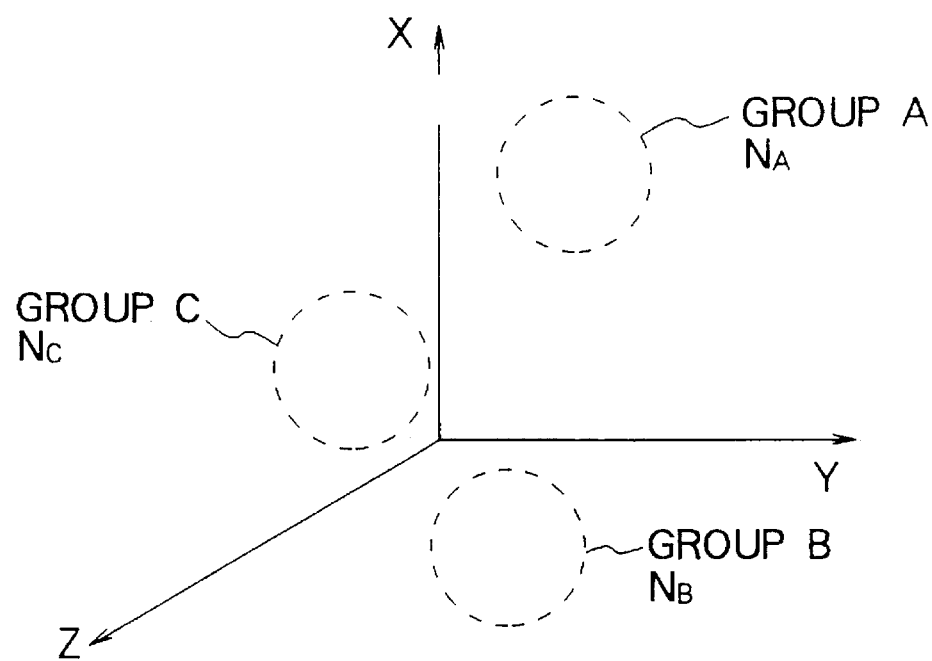
FIG. 8 illustrates the condition of a large number of foreign matter of the first embodiment of the present invention as plotted in the space formed by the coordinates axes of the composition ratio of each type of element.

FIG. 8 illustrates foreign matter, the number of which is n, that are plotted in the space formed by the coordinate axes of the elements X, Y, Z. In FIG. 8, foreign matters are categorized in to three groups which are respectively named group A, group B and group C. Group A includes foreign matter of which the number is $n_A$. Group B includes foreign matter of which the number is $n_B$. Group C includes foreign matter of which the number is $n_C$. The foreign matter can be classified such as above because the generating process of the foreign matter makes their composition ratio and element type be constant. Consequently, the scatter diagram of the principal components of FIG. 8 indicates that the foreign matter on the semiconductor wafer are generated in three processes. Thus, the foreign matter on the semiconductor wafer or on the surface of the semiconductor device pattern are usually generated from several kinds of generation sources. The foreign matter from these generation sources are distributed over the semiconductor wafer. Consequently, by investigating the composition ratio of the foreign matter included in one of several groups which are divided by the foreign matter classifying process section 11, identifying the process in which the foreign matters are generated becomes statistically possible.

The categorizing is performed concretely as follows.

Figure 9:
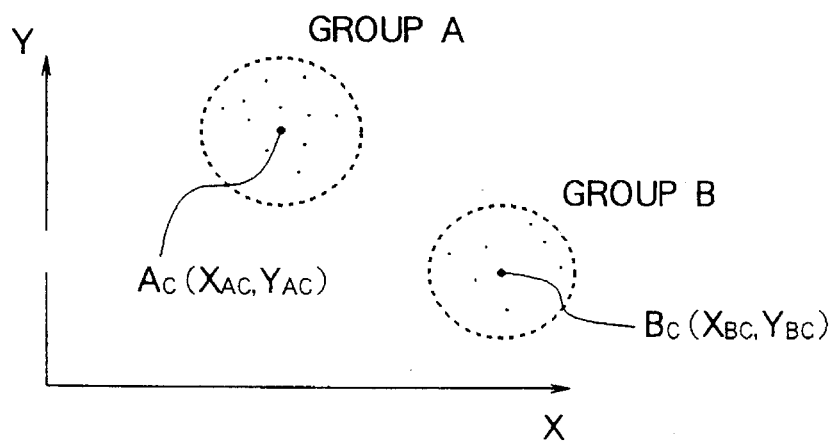
FIG. 9 is a scatter diagram of the principal components of foreign matter of the first embodiment of the present invention as an explanatory drawing of the classifying process.

For convenience of explanation, a case of X-Y coordinates being a two dimensional plane coordinates will be explained. FIG. 9 illustrates a scatter diagram of the principal component as a result of analysis. In the X-Y coordinates, much foreign matters is plotted and divided into group A and group B by type. The center coordinate of group A is given by $A_C$ ($X_{A\ C}, Y_{A\ C}$). The center coordinate of group B is given by $B_C$ ($X_{B\ C}, Y_{B\ C}$). Based on the scatter diagram of principal component, the number of such groups and the center coordinates for each group are obtained, and used for performing the categorization.

In order to obtain the number of groups and the center coordinates, the following process is performed.

Figure 10:
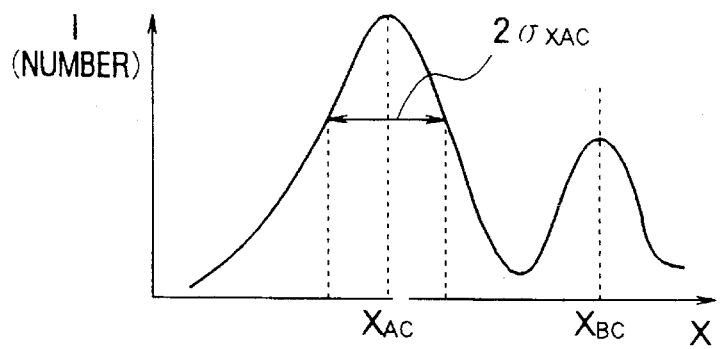
FIG. 10 is a distribution chart of the X axis elements of the foreign matter in the scatter diagram of the principal components illustrated in FIG. 9.

First, a distribution diagram of the foreign matter of the X axis such as FIG. 10 is required so as to obtain the number of groups and the center coordinates for X axis. In FIG. 10, the horizontal axis indicates the X axis and the vertical axis indicates the number of bits of foreign matter I. It is expected that the distribution illustrated in FIG. 10 is a normal distribution. Consequently, in the case of foreign matter divided into two groups such as group A and group B as illustrated in FIG. 9, the distribution illustrated in FIG. 10 consists of two normal distributions, one of which the center is $X_{A\ C}$ and the other of which the center is $X_{B\ C}$. Therefore, it is possible to obtain the number of groups of foreign matter and the center coordinates of the X axis of each group by investigating the peaks of the distribution illustrated in FIG. 10. It is also possible to obtain standard deviations $\sigma_{X\ A\ C}$ and $\sigma_{X\ B\ C}$ for the distributions of group A and group B respectively on the basis of the center coordinates $X_{A\ C}$ and $X_{B\ C}$ of the X axis as obtained above.

Figure 11:
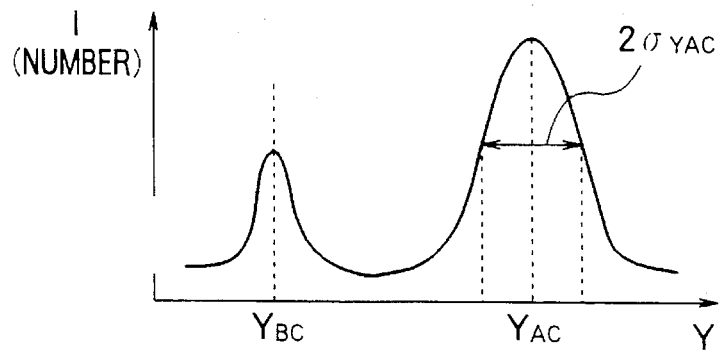
FIG. 11 is a distribution chart of the Y axis elements of the foreign matter in the scatter diagram of the principal components illustrated in FIG. 9.

Similarly, it is possible to obtain the number of groups of foreign matters, the center coordinates $Y_{A\ C}$ and $Y_{B\ C}$ of Y axis and the standard deviation $\sigma_{Y\ B\ C}$ and $\sigma_{Y\ B\ C}$ of the Y axis of each group by investigating the peaks of the distribution of foreign matter of the Y axis as illustrated in FIG. 11.

According to the above steps, the facts that the number of groups of foreign matters is two, that the center coordinates are $A_C (X_{A\ C}, Y_{A\ C})$ $B_C (X_{B\ C}, Y_{B\ C})$ and that the standard deviations are $(\sigma_{X A\ C}, \sigma_{Y A\ C})$, $(\sigma_{X B\ C}, \sigma_{Y B\ C})$ of the groups of the X axis and Y axis are confirmed. There may be cases wherein the number of groups of foreign matter of the X axis differs from the number of groups of the Y axis. This arises because the distributions of the groups overlaps each other in such a case, and so the largest number of the groups should be the number of the groups of all the foreign matter.

ST5

Identifying foreign matter type and the process which generates them.

The foreign matter identifying process section 12 identifies foreign matter type and the process which generates them on the basis of the center coordinates $A_C (X_{A\ C}, Y_{A\ C})$, $B_C (X_{B\ C}, Y_{B\ C})$ and the standard deviations $(\sigma_{X A\ C}, \sigma_{Y A\ C})$, $(\sigma_{X B\ C}, \sigma_{Y B\ C})$ of group A and group B of the X axis and Y axis.

Foreign matter type and the process which generates them can be somewhat predicted in advance. A data base concerning foreign matter type and the processes which generate them is stored in advance in the foreign matter data base 13.

The foreign matter identifying process section 12 compares the center coordinates of each group with the contents of a compounds table stored in the foreign matter data base 13, thereby identifying the foreign matter group.

More specifically, the process is performed as follows. The tables, of which the contents are the composition ratio coordinates $P_i(a_i,b_i)$ corresponding to foreign matter (where $a_i$ is the composition ratio of element X, $b_i$ is the composition ratio of element Y, i=1 to m ) of compounds, the number of which is m, are stored in foreign matter data base 13.

The foreign matter identifying process section 12 respectively calculates the distance between the center coordinates $A_C (X_{A\ C}, Y_{A\ C})$ of the foreign matter group A and each of the composition ratio coordinates $P_i (a_i,b_i)$ stored in the foreign matter data base 13, of which the number is m, then determines that the foreign matter $P_i$, which corresponds to the shortest of the calculated distances, is a foreign matter of this group A. The distance is defined as follows.

$$(X_{A\ C} - A_i)^2 + (Y_{A\ C} - b_i)^2$$

If the foreign matter is identified by the process described above, it is also possible to identify the process by which the foreign matter is generated based on the foreign matter data base 13. Thus, the foreign matter type and the process in which the foreign matter was generated are obtained.

ST6

The foreign matter identifying process section 12 outputs foreign matter type and the process by which the foreign matter was generated, as identified in above step ST5, and further outputs the number of foreign matter types classified by the foreign matter classifying process section 11 and the standard deviation of the distribution of the foreign matter, as the result of identifying the foreign matter. The result is displayed on a display unit not shown and is used for determining the quality of the manufacturing process of a semiconductor device.

As described above, according to embodiment 1 of the present invention, it is statistically and rapidly possible to analyze foreign matter types adhered to the surface of a semiconductor wafer or to the pattern of a semiconductor device and the process by which the foreign matter is generated.

Embodiment 1 of the present invention was explained using the results of analysis by the EPMA method. But the present invention is not limited to EPMA and can be adapted to use the analysis results of an Auger Electron Spectroscopy (AES) method which obtains spectral energy distribution of Auger electrons generated by an electron beam striking a test piece, a Secondary Ion Mass Spectroscopy (SIMS) method which performs mass spectrometry to analyze spattered secondary ions by an ion beam striking a test piece and so on, with similar effects being obtained.

In the diagram of an analyzing spectrum obtained by the AES method, the vertical axis indicates the number of Auger electrons and the horizontal axis indicates the energy of the electron beam. Also, in the diagram of an analyzing spectrum obtained by the SIMS method, the vertical axis indicates the ion count and the horizontal axis indicates the ion energy. Even if the coordinate axes of the analysis diagrams differ from those of the analysis diagrams of EPMA, the steps for obtaining element type and the composition ratio of the elements are the same as the steps in the case of the EPMA method.

Embodiment 2

In the foreign matter analyzing section described in embodiment 1 of the present invention, it is necessary for an analyst to input the coordinates of many foreign matters into a SEM 2 respectively after confirming the positions of the foreign matters on display section 3 and thereby obtain an analyzing spectrum of the foreign matter so as to analyze the foreign matter. But, as illustrated in FIG. 12, the present invention may also input the coordinates of the foreign matter automatically.

Figure 12:
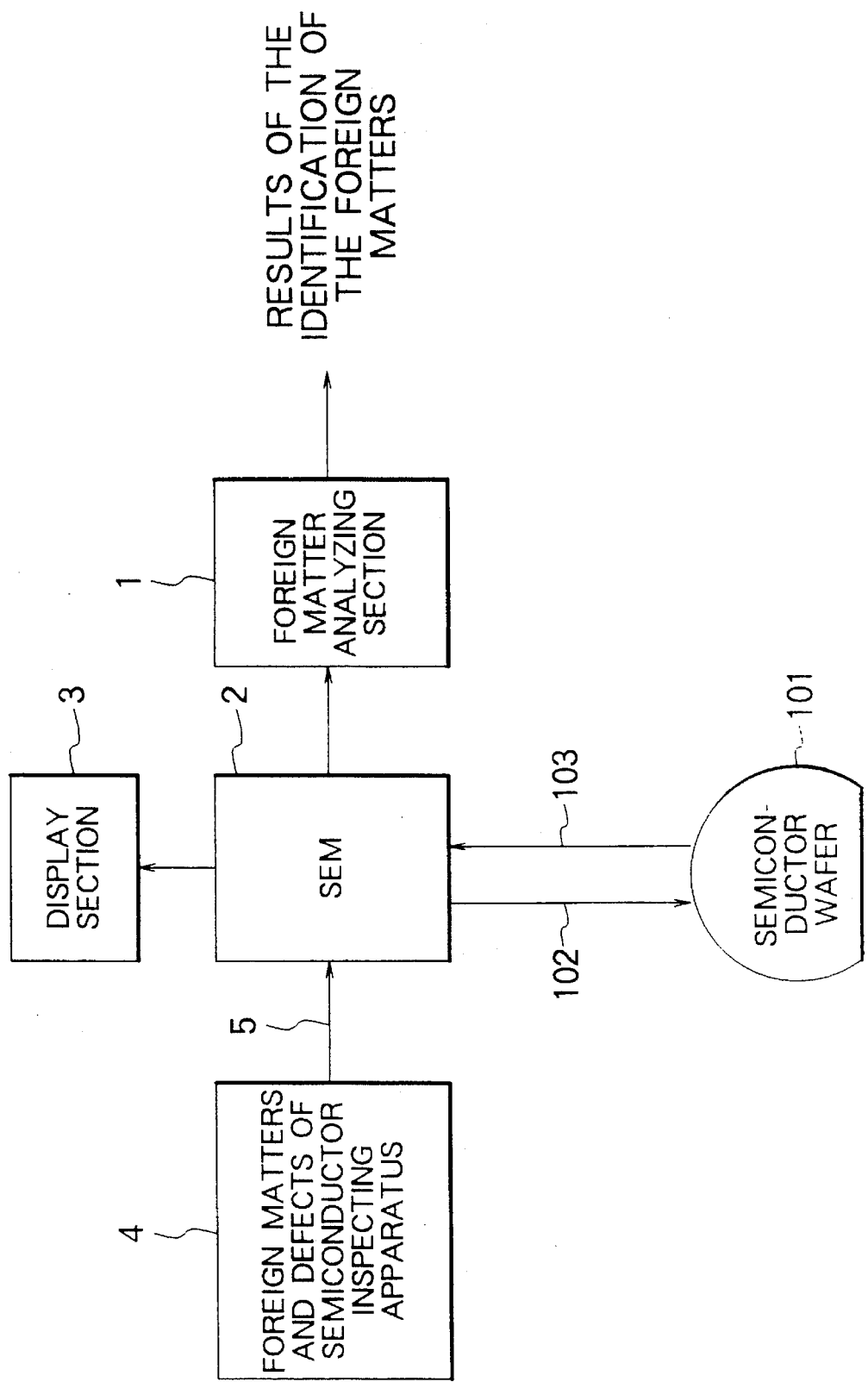
FIG. 12 is a block diagram of the foreign matter analyzing system of a second embodiment of the present invention.

FIG. 12 illustrates the construction of the foreign matter analyzing system according to embodiment 2 of the present invention. In FIG. 12, 4 denotes an apparatus for inspecting for foreign matter and defects of semiconductors which measures the position of foreign matter on the surface of semiconductor wafers or on the pattern of a semiconductor device, and outputs the coordinates 5 of the foreign matter. The inspecting apparatus 4 is the same as conventional one. The foreign matter analyzing section 1, SEM 2, display section 3, semiconductor wafer 101 and so on are the same as those illustrated in FIG. 1.

According to the foreign matter analyzing system illustrated in FIG. 12, SEM 2 performs EPMA analysis of foreign matter on the surface of semiconductor wafers or on the pattern of semiconductor device automatically on the basis of the coordinates 5 of the foreign matter outputed by the inspecting apparatus. 4. Consequently, an analyzer does not need to input the respective coordinates of the foreign matter and it is possible to improve working efficiency and to more quickly analyze and identify the process in which foreign matter is generated.

Embodiment 3

The analyzing apparatus described in embodiment 1 and embodiment 2 of the present invention can be applied to in-line measurement in the manufacturing process of a semiconductor device.

Figure 13:
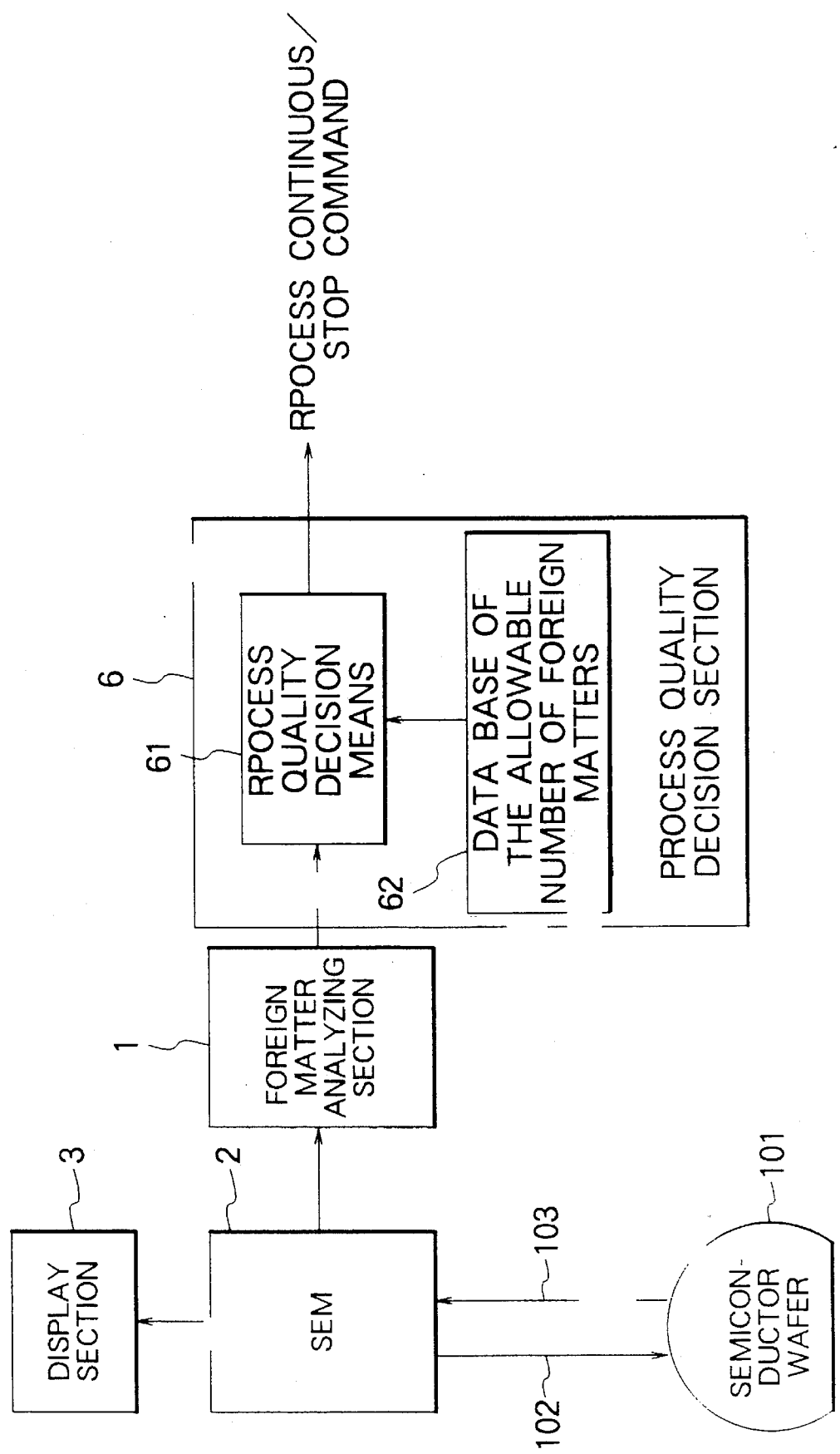
FIG. 13 is a block diagram of the foreign matter analyzing system of a third embodiment of the present invention.

FIG. 13 illustrates the construction of the control apparatus of a process for manufacturing semiconductors, which is used for the above purpose. In FIG. 13, the process quality decision section 6 decides the quality of the manufacturing process of a semiconductor device on the basis of the results of the identification of the foreign matter outputed by the foreign matter analyzing section 1. The process quality decision section 6 comprises a process quality decision means 61 which determines the quality of the process based on the results of the identification of the foreign matter, and a data base of the allowable number of foreign matters 62 in which the allowable number of foreign matter standard for determining quality is stored of each kind of foreign matter in advance. The foreign matter analyzing section 1, SEM 2, display section 3, semiconductor wafer 101 and so on are the same as those illustrated in FIG. 1.

Figure 14:
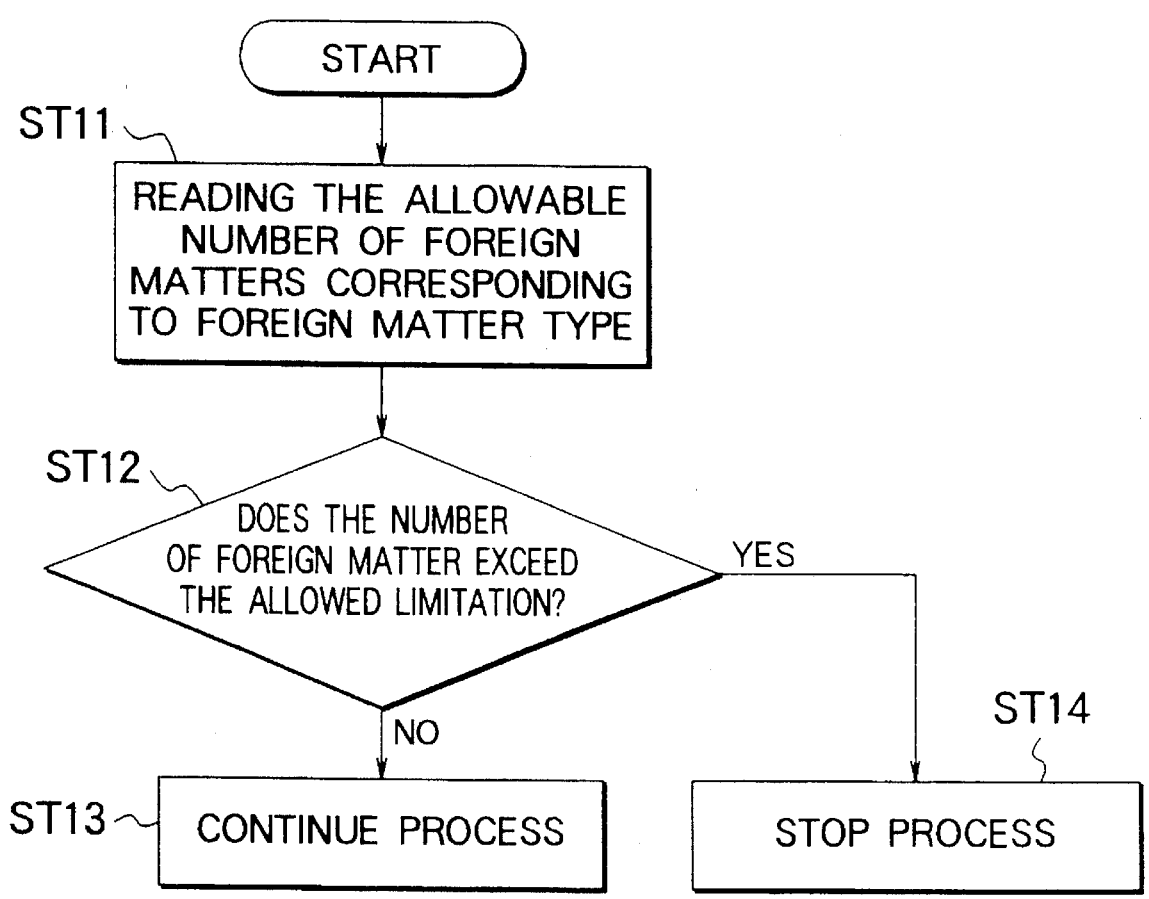
FIG. 14 is a flowchart for the quality decision process of the third embodiment of the present invention.
Figure 15:
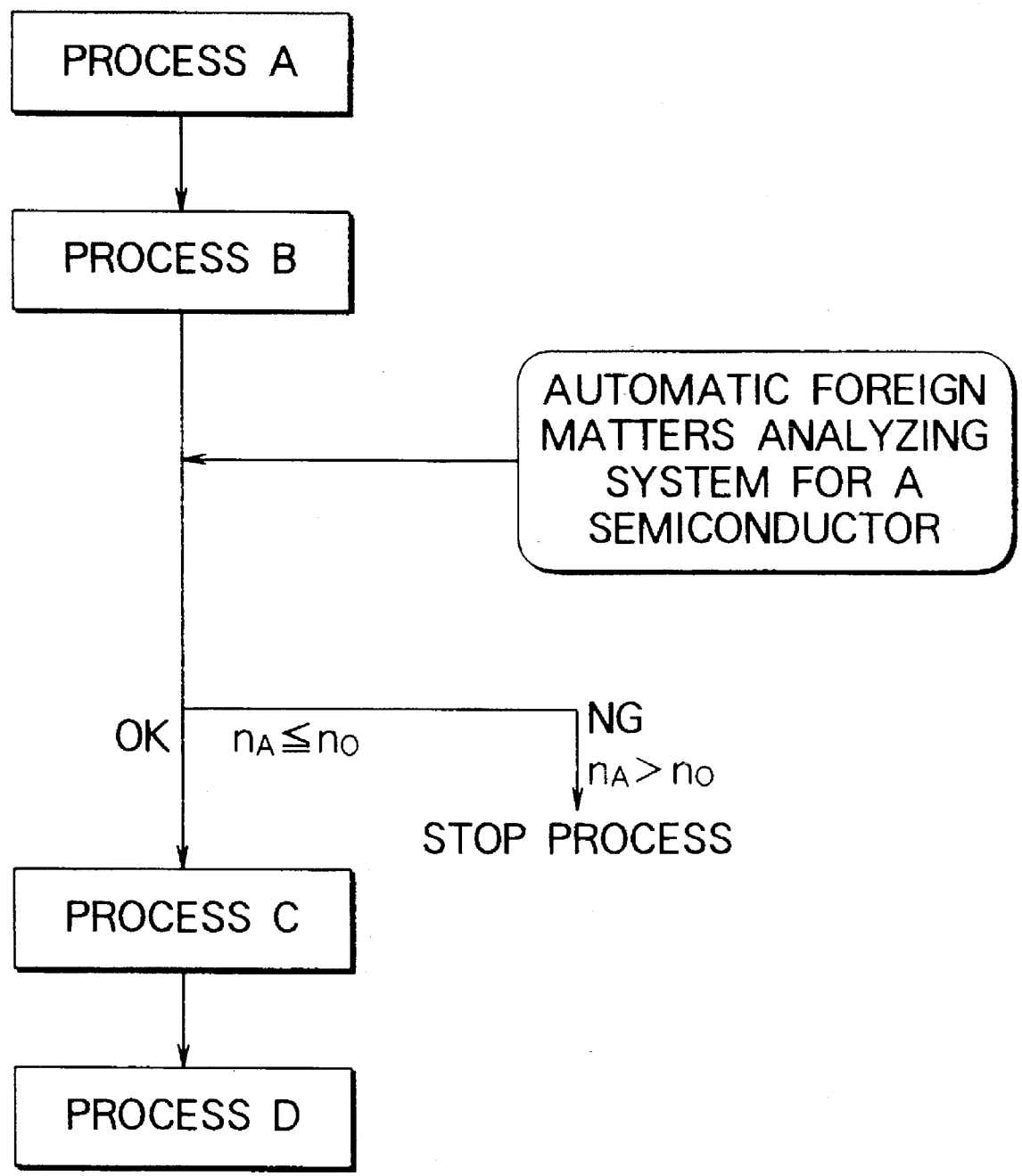
FIG. 15 is an explanatory drawing of the process of the third embodiment of the present invention.
Figure 16:
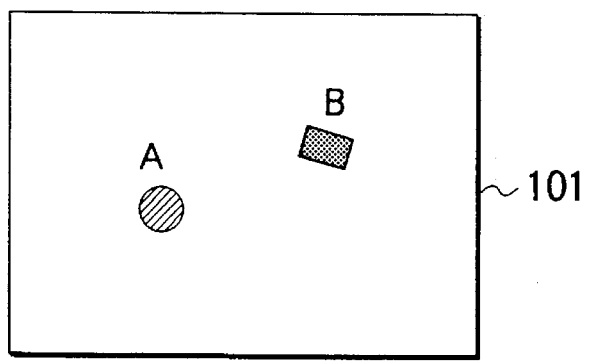
FIG. 16 is a secondary electron image observed by a Scanning Electron Microscope (SEM).
Figure 17:
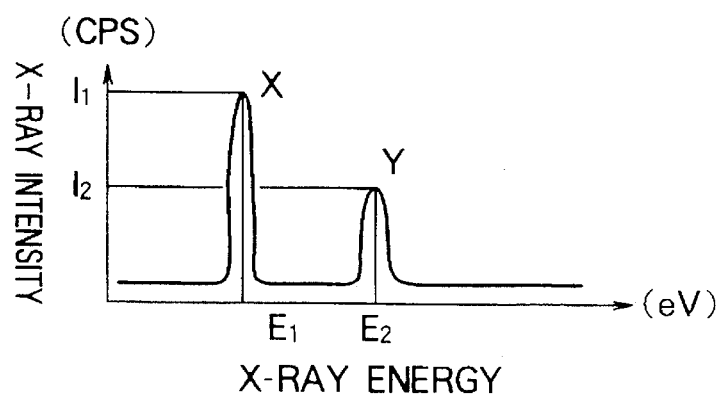
FIG. 17 illustrates an EPMA analysis spectrum of foreign matter A.
Figure 18:
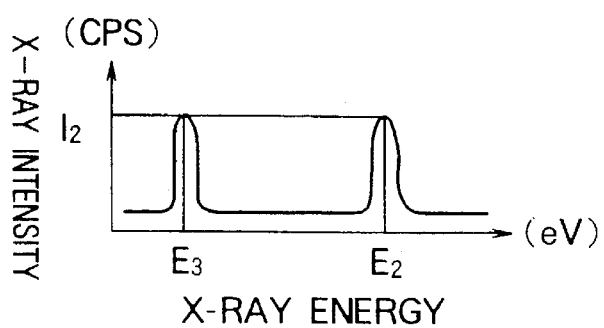
FIG. 18 illustrates an EPMA analysis spectrum of foreign matter B.

Next, the operation will be explained with reference to process quality decision flowchart in FIG. 14 and the explanatory chart of the manufacturing process in FIG. 15.

ST11

The process quality determining means 61 of the process quality decision section 6 reads the allowable number corresponding to foreign matter type of the analyzing section 1 from the data base of the allowed number of foreign matters 62. For example if, as illustrated in FIG. 8, the foreign matter is divided into three groups of A,B,C, then the number of foreign matter included in each group is $n_A, n_B, n_C$ respectively. The numbers $n_A, n_B, n_C$ are the numbers of foreign matter which are included within the range from the center of the distribution $(X_{A\ C}, Y_{A\ C})$, $(X_{B\ C}, Y_{B\ C})$, $(X_{C\ C}, Y_{C\ C})$ as illustrated in FIG. 8 to $(\sigma_{X_A\ C} + \sigma_{Y_A\ C})$, $(\sigma_{X_B\ C} + \sigma_{Y_B\ C})$, $(\sigma_{X_C\ C} + \sigma_{Y_C\ C})$ respectively, where $(\sigma_{X_A\ C} + \sigma_{Y_A\ C})$, $(\sigma_{X_B\ C} + \sigma_{Y_B\ C})$, $(\sigma_{X_C\ C} + \sigma_{Y_C\ C})$ are the standard deviations of the distributions of foreign matter.

The allowable number which is read from the data base of the allowable number of foreign matters 62 is $n_0$.

ST12

Next, it is decided whether the number of foreign matter exceeds the allowed limitation.

For example, if the value of $n_A$ is greater than that of $n_0$ ($n_A > n_0$), this process A is no good. Thus, the process quality decision section 6 decides to stop the process and the process proceeds to step ST14.

If this is not so ($n_A \leq n_0$), the process proceeds to step ST13, and the process continues.

ST14

If process A is determined to be no good, the semiconductor wafer corresponding to the decision is removed from the manufacturing line. The explanation chart of FIG. 15 conceptually illustrates the above process. In the manufacturing process comprising processes A to D, the quality of the processes A and B is determined for each semiconductor wafer after process B by using the automatic foreign matter analyzing system illustrated in FIG. 13. If the process is good (OK), the next processes C and D are performed. On the other hand, if the process is no good (NG), the process is stopped for this semiconductor wafer.

As described above, according to embodiment 3 of the present invention, in the manufacturing process of a semiconductor wafer, the quality of the process is decided for each semiconductor wafer and the process is continued only if the process is determined to be good. Thereby, it is possible to improve working efficiency and yield.

Embodiment 4

Although in the above description, an explanation is given of a case in which the number of the types of elements is 2 or 3, the present invention is applicable to cases in which the number of the types of elements is more than 4. In this case, if the number of the types of elements which compose the foreign matter is k (where k is an integer above 3), a foreign matter $P_i$ is plotted in coordinates $P_i(x_{i\ 1}, X_{i\ 2}, \ldots x_{i\ k})$ for example, where $x_{i\ 1}, x_{i\ 2}, \ldots x_{i\ k}$ are the composition ratio of the foreign matter.

It is possible to perform the analyzing process by using only measurement data extracted from data under some restrictions, for example, $x_{i\ 1} < r_0$, $x_{1\ 2} < r_1$, $\ldots x_{i\ k} < r_k$ (where $r_0$ to $r_k$ indicate predetermined restriction data). In this case, embodiment 4 of the present invention has an effect similar to the above embodiments 1 to 3. Furthermore, the number of the types of elements which should be processed decreases, and thereby the process can be performed easily and rapidly.

What is claimed is:

1. An analyzer for analyzing foreign matter comprising:

an analyzing section for obtaining composition ratios for each element of a plurality of foreign matter adhered to a semiconductor wafer;

a foreign matter distribution generation section for obtaining a distribution of each of the composition ratios of the plurality of foreign matter on the basis of a result obtained by said analyzing section;

a foreign matter classifying section for classflying the plurality of foreign matter on the basis of the distribution obtained by said foreign matter distribution generation section; and a foreign matter identifying section for comparing a result obtained by said foreign matter classflying section with predetermined foreign matter data, thereby identifying the foreign matter type.

2. The analyzer for analyzing foreign matter according to claim 1 further comprising:

a foreign matter inspecting section for obtaining positions of the plurality of foreign matter on the semiconductor wafers, respectively;

wherein said analyzing section analyzes a composition ratio of each element of the plurality of foreign matter on the basis of the positions output by said foreign matter inspecting section.

3. An apparatus for controlling the manufacturing of a semiconductor device comprising:

an analyzing section for obtaining composition ratios for each element of a plurality of foreign matter adhered to semiconductor wafers;

a foreign matter distribution generation section for obtaining a distribution of each of the composition ratios of the plurality of foreign matter on the basis of a result obtained by said analyzing section;

a foreign matter classifying section for classifying the plurality of foreign matter on the basis of the distribution obtained by said foreign matter distribution generation section;

a foreign matter identifying section for comparing a results obtained by said foreign matter classifying section with predetermined foreign matter data, thereby identifying the foreign matter type; and a determining section for comparing the number of foreign matter belonging to each type of the foreign matter identified by said foreign matter identifying section with predetermined number of allowable foreign matter data, thereby determining whether the semiconductor device manufacturing process should be continued.

4. A method for analyzing foreign matter comprising the steps of:

a first step of obtaining composition ratios for each element of a plurality of foreign matter adhered to semiconductor wafers;

a second step of obtaining a distribution for each composition ratio of the plurality of foreign matter on the basis of a result obtained by said first step;

a third step of classifying the plurality of foreign matter on the basis of the distribution obtained by said second step; and a fourth step of comparing a result obtained by said third step with predetermined foreign matter data, thereby identifying foreign matter type.

5. A method for analyzing foreign matter comprising the steps of:
- a first step of obtaining positions of a plurality of foreign matter on semiconductor wafers, respectively;
- a second step of obtaining composition ratios of each element of the plurality of foreign matter adhered to the semiconductor wafers;
- a third step of obtaining a distribution for each composition ratio of the plurality of foreign matter on the basis of a result obtained by said second step;
- a fourth step of classflying the plurality of foreign matter on the basis of the distribution obtained by said third step; and
- a fifth step for comparing a result obtained by said fourth step with predetermined foreign matter data, thereby identifying foreign matter type.

6. A method for controlling manufacturing process of a semiconductor device comprising the steps of:
- a first step of obtaining composition ratios of each element of a plurality of foreign matter adhered to semiconductor wafers;
- a second step of obtaining a distribution for each composition ratios of the plurality of foreign matters on the basis of a result obtained by said first step;
- a third step of classifying the plurality of foreign matter on the basis of the distribution obtained by said second step;
- a fourth step of comparing a result obtained by said third step with predetermined foreign matter data, thereby identifying foreign matter type; and
- a fifth step of comparing the number of foreign matter belonging to each type of foreign matter identified by said fourth step with predetermined number of allowable foreign matter data, thereby determining whether the semiconductor device manufacturing process should be continued.

* * * * *